US006423529B1

(12) United States Patent
Jain et al.

(10) Patent No.: US 6,423,529 B1
(45) Date of Patent: Jul. 23, 2002

(54) COMPOSITION USEFUL FOR THE EARLY DIAGNOSIS OF VISCERAL LEISHMANIASIS AND A PROCESS FOR PREPARING THE SAME

(75) Inventors: Girish Kumar Jain; Suman Tiwari; Suman Gupta; Jagdish Chandra Katiyar, all of Lucknow (IN)

(73) Assignee: Council of Scientific & Industrial Research, Lucknow (IN)

( * ) Notice: Subject to any disclaimer, the term of this patent is extended or adjusted under 35 U.S.C. 154(b) by 0 days.

(21) Appl. No.: 09/178,695

(22) Filed: Oct. 26, 1998

(30) Foreign Application Priority Data

Dec. 8, 1997 (IN) ........................................ 3518/Del/97

(51) Int. Cl.$^7$ ............................ C12N 1/00; C12N 5/00; C12N 5/02

(52) U.S. Cl. ........................ 435/243; 435/325; 435/374

(58) Field of Search ................................ 435/7.72, 243, 435/325, 374; 530/806

(56) References Cited

U.S. PATENT DOCUMENTS 5,069,910 A * 12/1991 Kovacic et al.
5,308,620 A * 5/1994 Yen

FOREIGN PATENT DOCUMENTS

| | | | |
|---|---|---|---|
| BR | 9302386 | | 1/1995 |
| EP | 0 997 734 | A1 | 5/2000 |
| WO | WO 93/00807 | | 1/1993 |
| WO | WO 95/11700 | | 5/1995 |

OTHER PUBLICATIONS

Ashford, R.W. et al., "Estimation of Population at Risk of Infection and Numbering of Cases of Leishmaniasis", *Parasitol. Today*, 8:104 (1992).

Berman, J.D. "Human Leishmaniasis: Clinical, Diagnostic, and Chemotherapeutic Developments in the Last 10 Years", *Clin. Infect. Dis.*, 24:684 (1997).

Bhatnagar, S. et al., "Exploration of antileishmanial activity in heterocycles; results of their in vivo & in vitro bioevaluations", *Ind. J. Med. Res.*, 89:439 (1989).

El Amin, E.R.M. et al., "ELISA using intact promastigotes for immunodiagnosis of kala–azar", *Trans. R. Soc. Trop. Med. Hyg.*, 79:344 (1985).

Gupta, S. et al., "a rising trend in kala–azar in Varanasi district, Uttar Pradesh, India: A recent survey using direct agglutinatin test", *Current Science*, 73:456 (1997).

Harith, A.E. et al., "Application of a Direct Agglutination Test for Detection of Specific Anti–Leishmania Antibodies in the Canine Reservoir", *J. Clin. Microbol.*, 27:2252 (1989).

Harith, A.E. et al., "A simple and economical direct agglutination test for serodiagnosis and sero–epidemiological studies of visceral leishmaniasis", *Trans. R. Soc. Trop. Med. Hyg*, 80:583 (1986).

Harith, A.E. et al., "Improvement of a Direct Agglutination Test for Field studies of Viseral Leishmaniasis", *J. Clin. Microbol.*, 26:1321 (1988).

Jaffe, C.L. et al., "Serodiagnostic assay for visceral leishmaniasis employing monoclonal antibodies", *Tran. R. Soc. Trop. Med. Hyg.*, 81:587 (1987).

Jahn, A. et al., "Evaluation of a visually read ELISA for serosiagnosis an sero–epidemiological studies of kala–azar in the Baringo District, Kenya", *Trans. R. Soc. Trop. Med. Hyg.*, 77:451 (1983).

Kohanteb, J. et al., "Detection of Leishmania donovani soluble antigen and antibody in the urine of visceral leishmaniasis patients", *Trans. R. Soc. Trop. Med. Hyg.*, 81:578 (1987).

Manning, M.C. et al., "Approaches for Increasing the Solution Stability of Proteins", *Biotechnology and Bioengineering*, 48:506 (1995).

Mengistu, G. et al., "The value of a direct agglutination test in the diagnosis of cutaneous and visceral leishmaniasis", *Trans R. Soc. Trop. Med. Hyg.*, 84:359 (1990).

Naik, S.R. et al., "Kala–azar in north–western India: A study of 24 patients", *Trans. R. Soc. Trop. Med. Hyg.*, 73:61 (1979).

Palatnik–De–Sousa, et al. "the FML vaccine (fucose–mannose ligand) protects hamsters from experimental Kala–azar", The Journal of the Brazilian Association for the Advancement of Science, vol. 46, No. 4, pp. 290–296 (1994).

* cited by examiner

*Primary Examiner*—Mark Navarro
(74) *Attorney, Agent, or Firm*—Foley & Hoag LLP

(57) ABSTRACT

This invention is relation to a composition useful for the early diagnosis of visceral leishmaniasis comprising trypsinised and commassie brilliant blue stained Leishmania promastigotes and a protein stabilising solute in the ratios ranging from 5 million: 0.0001 mg to 100 million: 1.00 mg.

10 Claims, No Drawings

COMPOSITION USEFUL FOR THE EARLY DIAGNOSIS OF VISCERAL LEISHMANIASIS AND A PROCESS FOR PREPARING THE SAME

FIELD OF THE INVENTION

This invention relates to a composition containing Leishmania promastigotes and a protein stabilizing solute useful for the early diagnosis of visceral leishmaniasis. Particularly, this invention relates to a composition containing *Leishmania donovani* promastigotes and a protein stabilising solute useful for the early diagnosis of visceral leishmaniasis or kala-azar. More particularly, the invention is useful for the early diagnosis of visceral leishmaniasis or Kala-azar in field conditions using Direct Agglutination Test (DAT) based on the composition of as disclosed herein.

BACKGROUND Of THE INVENTION

Visceral Leishmaniasis or Kala-azar, caused by an intracellular protozoan parasite Leishmania donovani, is transmitted from man to man through *Phlebotomus argentipes* (sand fly) of the phlebotomidae family.

The disease is geographically distributed in tropics and substropics of the world extending through most of the central and South East Asia, India, China, the Mediterranean region and Africa 90% of all the cases occur in Bangladesh, Brazil, India and sudan.

Visceral leishmaniasis is caused by *Leishmania donovani* in the Indian subcontinent and in East Africa, by *Leishmania infantum* in the mediterranean region and by *Leishmania chagasi* in the New World, mainly in Brazil, Peru and Paraguay (J. D. Berman; Clin. Infect. Dis., 24, 684, 1997).

It has been estimated that about 15 million people carry Leishmania infection (R. W. Ashford, P. Deszeux, P. deRadt; Parasitol. Today, 8, 104, 1992) and over 400,000 new cases appear each year. The number of people at risk is estimated to be 350 million in about 88 countires (Anon.; Tropical Disease, Leishmaniasis, 14, 1991 and F. Modabber; Tropical Disease Research Programme, Eleventh Programme Report, page 77, 1992). In India, in 1991 the disease had posed a great threat involving 38 out of the 42 districts of Bihar state, 8 districts of West Bengal and 2 districts of Eastern Uttar Pradesh (TDR News Letter, Published by UNDP/World Bank/WHO Special Programme for Research and Training in Tropical Diseases No. 36, 1991 and V. Srivastava; Ph.D. Thesis; Chemotherapy and Immunodiagnostic Investigations on Visceral Leishmaniasis, Agra University, Agra, India, 1992). From Bihar alone in 1991 the number of cases recorded were 2,50,000 with 2 to 3 thousand deaths and more than 4.5 lakh are directly exposed to the parasite (C. P. Thakur; Status Paper on Kala-azar in Bihar, Core group discussion on Kala-azar control in India, 24–25 September 1993). Sporadic cases have also been reported from Gujrat (F. B. W. Gajwani, A. Mehta, B. A. Sayed, N. N. Patel and R. S. Pandey; Ind. Med. Assoc., 49, 216, 1967), Kashmir (V.P. Jacob and S. L. Kalra; Ind. J. Med. Res., 39, 329, 1951), Himachal Pradesh (S. Gupta and R. S. Bhatia; Ind. Practitioner, 28, 609, 1975), Delhi (S. R. Naik, P. M. Rao, D. V. Dutta, S. Mehta, and P. N. Chuttani; Trans. R. Soc. Trop. Med. Hyg., 33, 61, 1979) and Uttar Pradesh (V. Srivastava; Ph.D. Thesis; Chemotherapy and Immunodiagnostic Investigations on Visceral Leishmaniasis, Agra University, Agra, India, 1992 and S. Gupta, S. Tiwari, A. K. Bagchi and J. C. Katiyar; Current Science 73,456, 1997)

The disease is characterized by irregular bouts of fever, often with loss of weight and appetite, hepatosplenomegaly, leucopenia, cachexia etc. If left untreated the fatality rate can be as high as 100%. In early stages the disease can be effectively treated with proper course of sodium stibogluconate (SSG) as there is little or no morbidity and no immunosuppression. At later stages disease is assoicated with many problems like greater morbidity, immunosuppression, secondary infection and drug resistance etc. and at this stage the patients respond poorly to various combinations of chemotherapy.

Keeping in view of these limitations, the essential component in the management. of the disease is the early detection and proper treatment with available chemotherapeutic agents.

Prior Art References

Till date, there is no suitable method for the diagnosis of Kala-azar particularly in early stages.

The definitive diagnosis of visceral leishmaniasis is based on demonstration of parasites in biopsies or aspirates of infected spleen, bone marrow and lymph nodes. Culture of aspirates from these locations is also sometimes successful. Both approaches suffer because of lack of adequate sensitivity when the load of organism is low. Spleen biopsy detects 90% active cases whereas bone marrow aspirate can detect 60-70% active cases. By lymph gland biopsy only 50-60% active cases can be detected. These procedures at times are hazardous, painful and labour extensive, require skilled hands, possible in hospitals only where results could be available at least 24 hours later, costly, fail to detect early and slight infective stage.

For Kala-azar, some of the non-specific tests which were in use in early days and being practiced even today at places include; Formal gel or Aldehyde test and Chopra's antimony test. They are also related to the level of IgG and positive results are also obtained when other causes of raised immunoglobulin levels are present whether of IgG or IgM classes. It is therefore a screening test, which, if positive, requires further investigations. The test is positive in about 85% of patients with VL. The test becomes positive about three months after the infection. So these tests may detect only symptomatic cases, they fail to detect early leishmaniasis.

Serological tests are a useful adjunct and are specially valuable in early or highly immune cases when amastigotes may be present in insufficient numbers to be seen easly. Besides, these tests have the advantages that the blood sampling is relatively easy and can be performed with little inconvenience to the patient and many samples may be processed simultaneously.

A battery of immunological procedures have been developed and they demonstrate antileishmanial antibodies for confirming clinical diagnosis. These include Indirect Immunofluorescent Antibody Test (C. L. Jaffe and D. McMahon Pratt.; Trans. R. Soc. Trop. Med. Hyg., 81, 587, 1987), Enzyme Linked Immunosborent Assay (A. Jahn and H. J. Diesfeld; Trans. R. Soc. Trop. Med. Hyg., 77, 451, 1983 and E. R. M. El Amin, E. P. Wright, P. A. Kager, J. J. Laarman and K. W. Pondman; Trans. R. Soc. Trop. Med. Hyg., 79, 344, 1985), Counter Current Immunoelectrophoresis (J. Kohanteb, S. M. Ardehali and M. R. Rijai; Trans. R. Soc. Trop. Med. Hyg., 81, 578, 1987) and Complement Fixation Test (M. G. Pappas, L. T. Canon, W. T. Hakmeyer and D. H. Smith; Ann. Trop. Med. Parasitol., 79, 147, 1985). However, some have low sensitivity, others are cross reactive and still others require elaborate laboratory facilities (IFA and RIA). Thus they do not meet the requirements of field test as mentioned below.

An ideal immunodiagnostic test should be simple, quick, specific and cheap, and be applicable in the fields even in the adverse conditions that prevail in many areas where leishmaniasis is endemic.

Direct Agglutination Test (A. E. Harith, A. H. Z. Kolk, P. A. Kager, J. Leeuwenburg, R. Muigai, S. Kingu and J. J. Laarman; Trans. R. Soc. Trop. Med. Hyg.; 80, 583, 1986 and A. E. Harith, A. H. Z. Kolk, J. Leeuwenburg, R. Muigai, E. Huigen, T. Jelsma and P. A. Kager; J. Clin. Microbiol.; 26, 1321, 1988) is promising in meeting these requirements. In DAT the antigen preparation consists of whole organism and the serological response to surface borne antigen is measured and the test could be performed on samples of whole blood, thus the difficulties of preparation and storage of serum, plasma and blood in filter paper are avoided. Allain and Kagan first described DAT (S. Allan and I. G. Kagan; Trop. Med. Hyg., 24, 332, 1975) for diagnosis of visceral leishmaniasis, Side 1986, DAT was modified and simplified to increase sensitivity and specificity and also comparisons were made with other serological tests. The test is also capable of detecting canine visceral leishmaniasis (A. E. Harith, R. J. Slappendel, I. Reiter, F. van Knappen, P. de Korte, E. Huigen and A. H. J. Kolk; J. Clin. Microbiol., 27, 2252, 1989) and diffused cutaneous leishmaniasis (G. Mengistu, R. Kisseling and H. Akuffo; Trans. R. Soc. Trop. Med. Hyg., 84, 359, 1990).

The studies have also demonstrated that while direct agglutination test (DAT) and enzyme linked immunosorbent assay (ELISA) have comparable diagnostic potentials, the former being more specific (S. Gupta, J.K. Srivastava, A. Pal, J. C. Katiyar, K. C. Saxena and B. N. Dhawan; Serodiag. Immunother. Infect. Dis., 6, 54, 1994) Besides, it neither requires sophisticated equipments/reagents nor high technical skill. The easy performance and the cost-effectivity adds to the merits of DAT for its acceptability for field use under Indian conditions.

The Direct Agglutination Test makes use of an aqueous suspension of trypsinized, Coomassie Brilliant Blue stained and formalized *Leishmania donovani* promastigotes, also referred as AQ Antigen or Liquid Antigen, for early diagnosis of visceral leishmaniasis. Preparation of aqueous antigen from other Leishmania species has also been reported in literature with a view to assess their comparable reactivity. Literature information reveals that there was no difference in titres obtained with antigen prepared from different Leishmania species (G. Mengistu, R. Kisseling and H. Akuffo; Trans. R. Soc. Trop. Med. Hyg., 84, 359, 1990). DAT is a fast and simple technique with a high sensitivity and specificity and, therefore, it is very suitable for use in field. One of the major drawback of the Liquid Antigen based DAT is its limited stability. Secondly,it suffers from the disadvantage that it has to be stored at 4° C., and a cold chain is required for its stability. The results are not repeated if the cold chain is disrupted at any point. The shaking during transportation also significantly affects the reproducibility of results with aqueous antigen. Therefore, when no cooling facilities are available and excessive road transportation is involved, as is often the case in the areas where leishmaniasis is frequently encountered, the availability of stable solid form of the antigen would facilitate the use of Direct Agglutination Test for the early diagnosis of visceral leishmaniasis in field conditions.

It was observed that the aqueous antigen on drying under high vaccum at room temperature produces a solid powder which does not show agglutination with *Leishmania donovani* antibodies and is, therefore, not useful in the early diagnosis of visceral leishmaniasis by direct agglutination test.

Similarly freezing the aqueous antigen at temperatures ranging from 0° C. to −196° C. and subsequently freeze drying the frozen antigen also results into a solid cake which also does not show any reactivity with *Leishmania donovani* antibodies and thus can not find use in early diagnosis of visceral leishmaniasis by direct agglutination test.

Thus, under the above mentioned conditions the aqueous antigen is undergoing denaturation rendering it inactive for early diagnosis of visceral leishamaniasis.

In the former case the denaturation of antigen may be taking place due to mechanical stresses produced under high vacuum in liquid state which may be producing non native conformation in dried state, whereas in the later case the major cause of loss in reactivity may be due to surface and freeze induced denaturation of protein present in *Leishmania donovani* antigen during freezing and freeze drying which again may be due to the formation of non native conformation in dry state.

Freeze induced denaturation of protein and antigen is a major concern in their development as pharmaceuticals and diagnostic tools. Freezing plays a crucial role in the damage incurred by the protein and antigens during freeze drying. The freeze induced denaturation of proteins and antigens is very closely related to surface induced denaturation and takes place mainly during the freezing and freeze drying process due to the stresses produced during these processes.

Freezing and freeze drying induced stresses, particularly cold temperatures, generation of large ice-water interface, exposure to concentrated solutes due to crystallization of water, crystallization of solutes and the resulting change in pH, are the main cause of denaturation of proteins and antigens which ultimately reduces the stability of the native state of proteins and antigens.

Since the preparation of *Leishmania donovani* antigen involves the use of whole organism and the serological response to surface borne antigen is measured in Direct Agglutination Test, it is highly important to protect the surface borne proteins from denaturation during freezing and subsequent freze drying process.

The freeze induced or surface induced denaturation of proteins and antigens can be inhibited by including protein stabilizing solutes in the compositions and formulations and the resistance to the stresses can be increased if the solution conditions are chosen that increase the thermodynamic stability of the native state of the proteins and antigens during freezing, freeze drying, storage and rehydration.

The requisite increase in free energy of denaturation during freezing and freeze drying can be achieved by adding requisite amount of protein stabilizing solutes to the proteins or antigens before initiating freezing or freeze drying. These solutes preferentially remain excluded from the surface of proteins at 25° C. but the stabilizing effect of these solutes is maintained during freezing and freeze drying and free energy of proteins and antigens is increased which increases the stability of the native state.

The protein stabilising solutes mainly include surface active agents, sugars, polyols, polymers, aminoacids and salts. The surface active agents have been broadly grouped as anionic, cationic and nonionic surface active agents. There are reports of stabilization of enzyme substrates and protein molecules by polyanion additives ( M. C. Manning, J. E. Matsuura, B. S. Kendrick, J. D. Meyer, J. J. Dormish, M. Vrkljan, J. R. Ruth, J. F. Carpenter and E. Shefter; Biotechnology and Bioengineering, 48, 506, 1995) but stabilization of *Leishmania donovani* antigen using any of such additive materials is hitherto not reported in literature.

During the course of the Applicants studies, it was observed that the surface and freeze induced denaturation of *Leishmania donovani* antigen is inhibited by the addition of small amounts of protein stabilising solutes, particularly anionic surfactants, more particularly sodium lauryl sulphate, which is hitherto not known in the literature. The addition of sodium lauryl sulphate presumably serves as water substitute and hydrogen bond to *Leishmania donovani* antigen thereby increasing its free energy during freezing thus increasing the stabiliy of the native antigen which is subsequently maintained during the process of freeze drying resulting in a solid freeze dried cake which is not only stable at room temperature but also shows similar order of reactivity with *Leishmania donovani* antibodies as is observed with aqueous antigen. This clearly indicates that freezing and subsequent freeze drying in presence of sodium lauryl sulphate results in preservation of native structure of the *Leishmania donovani* antigen through four distinct stages namely freezing, freeze drying, storage and rehydration. The solid cake composition thus produced is useful for early diagnosis of visceral Leishmaniasis under field conditions in endemic areas.

The comparison of Infra Red spectrum of *Leishmania donovani* aqueous antigen, *Leishmania donovani* antigen freeze dried without sodium layryl sulphate and *Leishmania donovani* antigen freeze dried with sodium lauryl sulphate revealed that the antigen freeze dried in presence of sodium lauryl sulphate maintains the native conformation of *Leishmania donovani* antigen during freezing, freeze drying and rehydration. It is quite evident from the amide-I region of the IR spectrum which particularly shows bands corresponding mainly to C=O stretching vibrations and to a lesser extent to C=N stretchings and C—C—N bending vibrations. This region is sensitive to small vibrations in molecular geometry, secondary structural compositions and hydrogen bonding Patterns within the proteins and antigenic substrates.

The IR spectrum of *Leishmania donovani* antigen freeze dried with sodium lauryl sulphate showed strong band at 1598 $cm^{-1}$ and a shoulder at 1675 $cm^{-1}$ where as IR spectrum of *Leishmania donovani* antigen without sodium lauryl sulphate showed appearence of an additional shoulder at 1625 $cm^{-1}$, decrease in intensity of band at 1675 $cm^{-1}$ and shifting of band at 1598 $cm^{-1}$ to 1594 $cm^{-1}$ The appearence of an additional shoulder at 1625 $cm^{-1}$ in *Leishmania donovani* antigen freeze dried without sodium lauryl sulphate may be assigned to alterations in secondary structures particularly to intermolecular B-sheet structure. Thus, the addition of sodium lauryl sulphate to *Leishmania donovani* antigen before freezing and freeze drying shows distinct protective effect in preserving the native conformation of the antigen.

Objects of the Invention

In order to overcome the problems associated with Aqueous Antigen or Liquid Antigen prepared from Leishmania promastigotes, the present invention provides a composition containing *Leishmania donovani* Promastigotes, *Leishmania infantum* Promastigotes and *Leishmania chagasi* Promastigotes, and a protein stabilising solute to stabilize *Leishmania donovani* promastigotes.

The main object of the present invention is to provide the *Leishmania donovani, Leishmania infantum* and *Leishmania chagasi* antigen in stable solid form in order to enhance its application potential even in unfavourable field conditions more particularly in endemic areas.

Another object of the present invention is to provide a composition containing *Leishmania donovani* promastigotes and a protein stabilising solute for the early diagnosis of visceral leishmaniasis which obviates the drawbacks as detailed above.

One more object of the invention is to provide the process for the preparing the above composition by freezing the solution at the temperature between 0 to 196° C., freeze drying the frozen solution at a temperature between 0 to −100° C. and storing freeze dried or lyophilized composition at a temperature between 18 to 45° C.

Still another object of the invention is to provide a composition containing *Leishmaia donovani* promastigotes and a protein stabilising solute which is in solid form.

Yet another object of the invention is to provide a composition containing *Leishmania donovani* promastigotes and a protein stabilising solute which is stable at room temperature.

Further object of this invention is to provide a composition containing *Leishmania donovani* promasigotes and a protein stabilising solute which is specific for diagnosis of *Leishmania donovani* infection by Direct Agglutination Test.

Still further object of this invention is to provide a composition containing *Leishmania donovani* promastigotes and a protein stabilising solute which does not show cross reactivity with antibodies present in serum samples of the patients from other diseases such as: Tuberculosis, Leprosy, Amoebiasis; Giardiasis, Malaria, Trypanosomiasis and Filariasis and other parasitic diseases.

Yet further object of this invention is to provide a composition containing *Leismania donovani* promastigotes and a protein stabilising solute which will serve as a convenient, rapid, simple economically feasible, sensitive and specific procedure for early diagnosis of *Leishmania donovani* infection in human cases under field conditions.

DETAILED DESCRIPTION OF THE INVENTION

Accordingly the present invention provides a composition containing *Leishmania donovani* promastigotes and a protein stabilising solute useful for early diagnosis of visceral leishmaniasis under field conditions prevalent in many countries. More particularly the present invention provides a process for the preparation of a composition containing *Leishmania donovani* promastigotes and a protein stabilising solute for the early diagnosis of visceral leishmaniasis which comprises : preparing aqueous antigen by known methods as herein described and treating the said aqueous antigen with the solution of protein stabilising solute in buffer, freezing the resulting solution, freeze drying or lyophilising the frozen solution and storing the brilliant blue coloured freeze dried or lyophilized composition in sterile glass containers or glass injection vials at ambient temperatures.

In an embodiment of the invention Leishmania promastigotes used for the preparation of antigen may be selected from *Leishmania donovani, Leishmania infantum* and *Leishmania chagasi.*

In another embodiment of the invention each one ml of aqueous antigen may contain *Leishmania promastigotes* in the range of 0.5 million to 100 million.

In yet another embodiment of the invention the composition may contain *Leishmania promastigotes* and the protein stabilising solute in the ratios ranging from of 5 million : 0.0001 mg to 100 million : 1.00 mg.

In another embodiment of the invention the buffers used may be such as physiological saline or citrate saline.

In another embodiment of the invention the freeze drying temperature of the frozen solution containing *Leishmania donovani* aqueous antigen and protein stabilising solute may be in the range of 0° C. to −100° C.

The most preferred embodiment of this invention resides in Freze-Dried *Leishmania donovani* Promastigote composition comprising Trypsinized Coomassie Brilliant Blue stained *Leishmania donovani* Promastigote and a protein stabilizing solute.

In yet another embodiment of the invention the suitable protein stabilizing solute used may be selected from the following compounds: Anionic Surfactants, Cationic Surfactants, Nonionic Surfactants including Glycyl esters, glyceryl esters, monoglycerides, diglycerides, mono and diesters of propylene glycol, macrogol esters, macrogol ethers, lauromacrogols, polyoxyl esters, nonoxynols, octoxynols, tyloxapols, poloxamers, polysorbates, monosorbitan esters, disorbitan esters, benzalkonium halides, Benzododecinium halides, bithionol, cetalkonium halides, cethexonium halides, cetylpyridinium halides, docusate calcium, docusate potassium, docusate sodium, sodium cetostearyl sulphate, sodium lauryl sulphate, sodium dodecyl sulphate, sodium oleate, sodium ricinoleate, sodium tetradecyl sulphate, sodium hexadecyl sulphate, polyoxyethylene-9-lauryl ethers, glycerol, ethylene glycol, polyethylene glycols in molecular range of 300 to 6000, polyvinyl pyrrolidone, sodium glutamate, sodium thiocyanate, 2-bromo-2-nitro-1,3-propanediol, glucose, trehalose, sucrose fatty acid monoesters, sucrose, and cyclodextrins including beta cyclodextrin, hydroxy propyl beta cyclodextrin. The most preferred protein stabilising solutes are sodium lauryl sulphate or sodium dodecyl sulphate or sucrose individually or in a suitable combination with other stabilising solutes.

To use the Composition of the invention, the composition equivalent to 0.5 million to 100 million promastigotes is taken in 10 ul to 100 ul of citrate saline buffer containing 0.1 ul to 100 ul of 0.01% to 1% formalin solution in citrate saline and added to 10 ul to 100 ul of test serum sample, placed in V-shaped well microtitre plates. The contents are mixed well and kept at 18° C. to 22° C. for 2-20 hrs and the results of agglutination are read visually against a white back ground. A titre of 1:3200 or more was considered positive. The results are compared with control pool positive and pool negative sera. The composition did not show any cross reactivity with sera from patients with other diseases like tuberculosis, leprosy, amoebiasis, giardiasis, malaria, filariasis and echinococcosis, hepatitis-B, typhoid, AIDS and trypanosomiasis. The dignostic tests can be carried out by those with ordinary skill in the art.

Aqueous Antigen or Liquid antigen is prepared by culturing spleen tissue (A. E. Harith, A. H. J. Kolk, P. A. Kager, J. Leeuwenburg, R. Muigai, S. Kiugu, S. Kiugu and J. J. Laarman; Trans. R. Soc. Trop. Med. Hyg., 80, 583, 1986) or bone marrow aspirate (S. Bhatnagar, S. C. Moitra, P. Y. Guru and J. C. Katiyar; Ind. J. Med. Res., 89, 439, 1989) from infected hamster. In brief, in-vitro, *Leishmania donovani* promastigotes were primarily grown by culturing infected hamster's spleen tissue in biphasic NNN medium at 26° C.±1° C. for 10 to 15 days. At every 7-8 days, Serial sub cultures of promastigotes are done by inoculating the biphasic NNN medium, consisting of 2 ml of NNN Medium and 2 ml of RPMI 1640 overlay medium with $1\times10^6$ to $1.5\times10^6$ million promastigotes. For bulk cultivation the promastigotes from NNN/RPMI 1640 medium are grown in L-15 monophasic medium containing 10% Foetal Calf Serum. Parasites are harvested when a vast majority of promastigote population attains elongated form and their concentration reaches about $40\times10^6$ promastigote per ml of the medium. The culture is centrifuged for 15 minutes at 4000 g at 4° C. The pellet formed after centrifugation is washed five times by centrifugation with 200 equal volumes of cold Locke's solution at 3200 g at 4° C. for 10 minutes. One packed volume of promastigotes is treated with 20 equal volumes of 0.2% trypsin in Locke's solution (pH 7.2) for 45 minutes at 37° C. and then centrifuged at 3200 g at 4° C. and washed five times as above. The pellet is then suspended in cold Locke's solution so as to obtain a concentration of $200\times10^6$ promastigotes per ml. An equal volume of cold 2% formaldehyde in Locke's solution is added and left at 4° C. for 20 hours for fixation. The promastigotes are then centrifuged at 3200 g and washed with cold citrate saline. These promastigotes are stained with 0.1% (w/v) coomassie brilliant blue in citrate saline for 90 minutes using a magnetic stirrer at a moderate speed. The stained parasites are then centrifuged and washed twice with citrate saline and the pellet is resuspended in citrate saline in such a way so as to obtain the Aqueous Antigen Suspension having 5 million to 100 million promastigotes per ml.

The details of the invention are given in the example provided below which are given by way of illustrations only and therefore, should not be construed to limit the scope of the present invention.

EXAMPLE 1

Preparation of AO Antigen or Liquid Antigen

In-vitro, *Leishmania donovani* promastigotes were primarily grown by culturing infected hamster's spleen tissue in biphasic NNN medium at 26° C.±1° C. for 10 to 15 days. At every 7-8 days, Serial sub cultures of promastigotes are done by inoculating 4 ml of biphasic NNN medium, consisting of 2 ml of NNN Medium and 2 ml of RPMI 1640 Overlay Medium with $1\times10^6$ to $1.5\times10^6$ million promastigotes. Bulk cultivation of the promastigotes is done by inoculating 3 ml of NNN/RPMI 1640 sub culture containing $5\times10^6$ promastigotes per ml in 50 ml of L-15 monophasic medium containing 10% Foetal Calf Serum. Parasites are harvested when a vast majority of promastigote population attains elongated form and their concentration reaches about $40\times10^6$ promastigote per ml of the medium. The culture is centrifuged for 15 minutes at 4000 g at 4° C. The pellet formed after centrifugation is washed five times by centrifugation with 200 equal volumes of cold Locke's solution at 3200 g at 4° C. for 10 minutes. One packed volume of promastigotes is treated with 20 equal volumes of 0.2% trypsin in Locke's solution (pH 7.2) for 45 minutes at 37° C. and then centrifuged at 3200 g at 4' C. and washed five times as above. The pellet is then suspended in cold Locke's solution so as to obtain a concentration of $200\times10^6$ promastigotes per ml. An equal volume of cold 2% formaldehyde in Locke's solution is added and left at 4° C. for 20 hours for fixation. The promastigotes are then centrifuged at 3200 g and washed with cold citrate saline. These promastigotes are stained with 0.1% (w/v) coomassie brilliant blue in citrate saline for 90 minutes using a magnetic stirrer at a moderate speed. The stained parasites are then centrifuged and washed twice with citrate saline and the pellet is resuspended in citrate saline in such a way so as to obtain the Aqueous Antigen Suspension having 48-50 million promastigotes per ml Preparation of The Composition 1 ml aliquots of Aqueous antigen with a promastigote count of 48 to 50 million, are taken in sterile glass injection vials or in sterile screw cap glass vials. To the above aliquots is added 100 ul of 0.3% sterile solution of sodium lauryl sulphate in citrate saline buffer. The contents are mixed homogeneously, the resulting solution is frozen at −30° C. and freeze dried or lyophilised at −50° C. to get freeze dried or lyopbilised antigen composition as a brilliant blue coloured solid cake. The resulting freeze dried composition is sealed under vacuum or stored aseptically in air tight containers at ambient temperature. All the experimental operations are carried out with sterile medium and sterile reagent solutions under aseptic conditions.

Diagnosis of Visceral Leishmaniasis

Test serum samples were serially diluted double fold (1:200 to 1:1,28,000) with 0.2% gelatin and 0.78% P-mercaptoethanol in physiological saline and 50 ul of these dilutions were placed in V-shaped well microtitre plates leaving the first well of the plate as antigen control containing 50 ul of only gelatin saline solution.

The Freeze Dried composition equivalent to 2.4 to 2.5 million promastigotes is taken in 50 ul of citrate saline buffer containing 0.25 ul of 1% solution of formaldehyde in citrate saline and added to 50 ul of test serum samples placed in V-shaped well microtitre plates. The contents are mixed well and kept at 22° C. for 12 hrs and the results are read visually against a white back ground. A titre of 1:3200 or more was considered positive. The results are compared with control pool positive and pool negative sera. The test serum samples from patients suffering from visceral leishmaniasis show agglutination while serum samples from patients sufferring from tuberculosis, leprosy, amoebiasis, giardiasis, malaria, filariasis and trypanosomiasis did not show any sign of agglutination. The diagnostic test can be carried out by any one with ordinary skill in the art.

EXAMPLE 2

Preparation of AO Antigen or Liquid Antigen

In-vitro, *Leishmania donovani* promastigotes were primarily grown by culturing infected hamster's spleen tissue in biphasic NNN medium at 26° C.±1° C. for 10 to 15 days. At every 7-8 days, Serial sub cultures of promastigotes are done by inoculating the biphasic NNN medium, consisting of 2 ml of NNN Medium and 2 ml of RPMI 1640 Overlay Medium, with $1\times10^6$ to $1.5\times10^6$ million promastigotes. Bulk cultivation of the promastigotes is done by inoculating 3 ml of NNN/RPMI 1640 sub culture containing $5\times10^6$ promastigotes per ml in 50 ml of L-15 monophasic medium containing 10% Foetal Calf Serum. Parasites are harvested when a vast majority of promastigote population attains elongated form and their concentration reaches about $40\times10^6$ promastigote per ml of the medium. The culture is centrifuged for 15 minutes at 4000 g at 4° C. The pellet formed after centrifugation is washed five times by centrifugation with 200 equal volumes of cold Locke's solution at 3200 g at 4° C. for 10 minutes. One packed volume of promastigotes is treated with 20 equal volumes of 0.2% trypsin in Locke's solution (pH 7.2) for 45 minutes at 37° C. and then centrifuged at 3200 g at 4° C. and washed five times as above. The pellet is then suspended in cold Locke's solution so as to obtain a concentration of $200\times10^6$ promastigotes per ml. An equal volume of cold 2% formaldehyde in Locke's solution is added and left at 4° C. for 20 hours for fixation. The promastigotes are then centrifuged at 3200 g and washed with cold citrate saline. These promastigotes are stained with 0.1% (w/v) coomassie brilliant blue in citrate saline for 90 minutes using a magnetic stirrer at a moderate speed. The stained parasites are then centrifuged and washed twice with citrate saline and the pellet is resuspended in citrate saline in such a way so as to obtain the Aqueous Antigen Suspension having 48-50 million promastigotes per ml.

Preparation of Composition 1 ml aliquots of Aqueous Antigen with a promastigote count of 48 to 50 million are taken in sterile glass injection vials or sterile screw cap glass vials. To the above aliquots is added 100 ul of 0.3% sterile solution of Sodium dodecyl sulphate in citrate saline buffer. The contents are mixed homogeneously, the resulting solution is frozen at −30° C. and freeze dried or lyophilised at −50° C. to get freeze dried or lyophilised antigen composition as a brilliant blue coloured solid cake. The freeze dried composition is sealed under vacuum or stored aseptically in air tight containers at ambient temperature. All the experimental operations are carried out with sterile medium and sterile reagent solutions under aseptic conditions.

Diagnosis of Visceral Leishmaniasis

Test serum samples were serially diluted double fold (1:200 to 1:1,28,000) with 0.2% gelatin and 0.78% B-mercaptoethanol in physiological saline and 50 ul of these dilutions were placed in V-shaped well microtitre plates leaving the first well of the plate as antigen control containing 50 ul of only gelatin saline solution.

The Freeze Dried composition equivalent to 2.4 to 2.5 million promastigotes is taken in 50 ul of citrate saline buffer containing 0.25 ul of 1% solution of formaldehyde in citrate saline and added to 50 ul of test serum samples placed in V-shaped well microtitre plates. The contents are mixed well and kept at 22° C. for 12 hrs and the results are read visually against a white back ground. A titre of 1:3200 or more was considered positive. The results are compared with control pool positive and pool negative sera. The test serum samples from patients suffering from visceral leishmaniasis show agglutination while serum samples from patients sufferring from tuberculosis, leprosy, amoebiasis, giardiasis, malaria, filariasis and trypanosomiasis did not show any sign of agglutination. The diagnostic test can be carried out by any one with ordinary skill in the art.

EXAMPLE 3

Preparation of AO Antigen or Liquid Antigen

In-vitro, *Leishmania donovani* promastigotes were primarily grown by culturing infected hamster's spleen tissue in biphasic NNN medium at 26° C.±1° C. for 10 to 15 days. At every 7-8 days, Serial sub cultures of promastigotes are done by inoculating the biphasic NNN medium, consisting of 2 ml of NNN Medium and 2 ml of RPMI 1640 Overlay Medium, with $1\times10^6$ to $1.5\times10^6$ million promastigotes. Bulk cultivation of the promastigotes is done by inoculating 3 ml of NNN/RPMI 1640 sub culture containing $5\times10^6$ promastigotes per ml in 50 ml of L-15 monophasic medium containing 10% Foetal Calf Serum. Parasites are harvested when a vast majority of promastigote population attains elongated form and their concentration reaches about $40\times10^6$ promastigote per ml of the medium. The culture is centrifuged for 15 minutes at 4000 g at 4° C. The pellet formed after centrifugation is washed five times by centrifugation with 200 equal volumes of cold Locke's solution at 3200 g at 4° C. for 10 minutes. One packed volume of promastigotes is treated with 20 equal volumes of 0.2% trypsin in Locke's solution (pH 7.2) for 45 minutes at 37° C. and then centrifuged at 3200 g at 4° C. and washed five times as above. The pellet is then suspended in cold Locke's solution so as to obtain a concentration of $200\times10^6$ promastigotes per ml. An equal volume of cold 2% formaldehyde in Locke's solution is added and left at 4° C. for 20 hours for fixation. The promastigotes are then centrifuged at 3200 g and washed with cold citrate saline. These promastigotes are stained with 0.1% (w/v) coomassie brilliant blue in citrate saline for 90 minutes using a magnetic stirrer at a moderate speed. The stained parasites are then centrifuged and washed twice with citrate saline and the pellet is resuspended in citrate saline in such a way so as to obtain the Aqueous Antigen Suspension having 48-50 million promastigotes per ml.

Preparation of Composition 1 ml aliquots of Aqueous Antigen with a promastigote count of 48 to 50 million, are taken in sterile glass injection vials or sterile screw cap glass vials. To the above aliquots is added 100 ul of 0.3% sterile solution of Sodium lauryl sulphate in citrate saline buffer and 100 ul of 0.3% sterile sucrose solution in citrate saline buffer. The contents are mixed homogeneously, the resulting solution is frozen at −30° C. and freeze dried or lyophilised at −50° C. to get freeze dried or lyophilised antigen composition as a brilliant blue coloured solid cake. The resulting freeze dried composition is sealed under vacuum or stored aseptically in air tight containers at ambient temperature. All the experimental operations are carried out with sterile medium and sterile reagent solutions under aseptic conditions.

Diagnosis of Visceral Leishmaniasis

Test serum samples were serially diluted double fold (1:200 to 1:1,28,000) with 0.2% gelatin and 0.78% P-mercaptoethanol in physiological saline and 50 ul of these dilutions were placed in V-shaped well microtitre plates leaving the first well of the plate as antigen control containing 50 ul of only gelatin saline solution.

The Freeze Dried composition equivalent to 2.4 to 2.5 million promastigotes is taken in 50 ul of citrate saline buffer containing 0.25 ul of 1% solution of formaldehyde in citrate saline and added to 50 ul of test serum samples placed in V-shaped well microtitre plates. The contents are mixed well and kept at 22° C. for 12 hrs and the results are read visually against a white back ground. A titre of 1:3200 or more was considered positive. The results are compared with control pool positive and pool negative sera. The test serum samples from patients suffering from visceral leishmaniasis show agglutination while serum samples from patients sufferring from tuberculosis, leprosy, amoebiasis, giardiasis, malaria, filariasis and trypanosomiasis did not show any sign of agglutination. The diagnostic test can be carried out by any one with ordinary skill in the art.

EXAMPLE 4

Preparation of AO Antigen or Liquid Antigen

In-vitro, *Leishmania donovani* promastigotes were primarily grown by culturing infected hamster's spleen tissue in biphasic NNN medium at 26° C.±1° C. for 10 to 15 days. At every 7-8 days, serial sub cultures of promastigotes are done by inoculating the biphasic NNN medium, consisting of 2 ml of NNN Medium and 2 ml of RPMI 1640 Overlay Medium, with $1\times10^6$ to $1.5\times10^6$ million promastigotes. Bulk cultivation of the promastigotes is done by inoculating 3 ml of NNN/RPMI 1640 sub culture containing $5\times10^6$ promastigotes per ml in 50 ml of L-15 monophasic medium containing 10% Foetal Calf Serum. Parasites are harvested when a vast majority of promastigote population attains elongated form and their concentration reaches about $40\times10^6$ promastigote per ml of the medium. The culture is centrifuged for 15 minutes at 4000 g at 4° C.. The pellet formed after centrifugation is washed five times by centrifugation with 200 equal volumes of cold Locke's solution at 3200 g at 4° C. for 10 minutes. One packed volume of promastigotes is treated with 20 equal volumes of 0.2% trypsin in Locke's solution (pH 7.2) for 45 minutes at 37° C. and then centrifuged at 3200 g at 4° C. and washed five times as above. The pellet is then suspended in cold Locke's solution so as to obtain a concentration of $200\times10^6$ promastigotes per ml. An equal volume of cold 2% formaldehyde in Locke's solution is added and left at 4° C. for 20 hours for fixation. The promastigotes are then centrifuged at 3200 g and washed with cold citrate saline. These promastigotes are stained with 0.1% (w/v) coomassie brilliant blue in citrate saline for 90 minutes using a magnetic stirrer at a moderate speed. The stained parasites are then centrifuged and washed twice with citrate saline and the pellet is resuspended in citrate saline in such a way so as to obtain the Aqueous Antigen Suspension having 48-50 million promastigotes per ml.

Preparation of Composition 1 ml aliquots of Aqueous Antigen with a promastigote count of 48 to 50 million, are taken in sterile glass injection vials or sterile screw cap glass vials. To the above aliquots is added 100 ul of 0.3% sterile sucrose solution in citrate saline buffer. The contents are mixed homogeneously, the resulting solution is frozen at −30° C. and freeze dried or lyophilised at −50° C. to get freeze dried or lyophilised antigen composition as a brilliant blue coloured solid cake. The resulting freeze dried product is sealed under vacuum or stored aseptically in air tight containers at ambient temperature. All the experimental operations are carried out with sterile medium and sterile reagent solutions under aseptic conditions.

Diagnosis of Visceral Leishmaniasis

Test serum samples were serially diluted double fold (1:200 to 1:1,28,000) with 0.2% gelatin and 0.78% 1-mercaptoethanol in physiological saline and 50 ul of these dilutions were placed in V-shaped well microtitre plates leaving the first well of the plate as antigen control containing 50 ul of only gelatin saline solution.

The Freeze Dried composition equivalent to 2.4 to 2.5 million promastigotes is taken in 50 ul of citrate saline buffer containing 0.25 ul of 1 solution of formaldehyde in citrate saline and added to 50 ul of test serum samples placed in V-shaped well microtitre plates. The contents are mixed well and kept at 22° C. for 12 hrs and the results are read visually against a white back ground. A titre of 1:3200 or more was considered positive. The results are compared with control pool positive and pool negative sera. The test serum samples from patients suffering from visceral leishmaniasis show agglutination while serum samples from patients sufferring from tuberculosis, leprosy, amoebiasis, giardiasis, malaria, filariasis and trypanosomiasis did not show any sign of agglutination. The diagnostic test can be carried out by any one with ordinary skill in the art.

What is claimed is:

1. A composition useful for the early diagnosis of visceral leishmaniasis comprising trypsinised and coomassie brilliant blue stained leishmania promastigotes and a protein stabilising solute having a ratio of promastigotes: protein stabilising solute between 5 million: 0.0001 mg to 100 million: 1.00 mg.

wherein the composition is a solid and the protein stabilising solute selected from the group consisting of surface active agents, sugars, polyols, polymers and amino acids.

2. A composition as claimed in claim 1 wherein one ml aqueous antigen contains Leishmania promastigotes in the range of 0.5 million to 100 million.

3. A composition as claimed in claim 1, further comprising buffers such as physiological saline or citrate saline.

4. A composition as claimed in claim 1, wherein the protein stabilising solute used is selected from anionic surfactants, cationic surfactants, non-ionic surfactants including glycyl esters, glyceryl esters, monoglycerides, diglycerides, mono and diesters of propylene glycol, macrogol esters, macrogol ethers, lauromacrogols, polyoxyl esters, nonoxynols, octoxynols, tyloxapols, poloxamers, polysorbates, monosorbitan esters, disorbitan esters, benzalkonium halides, Benzododecinium halides, bithionol, cetalkonium halides, cethexonium halides, cetylpyridinium halides, docusate calcium, docusate potassium, docusate sodium, sodium cetostearyl sulphate, sodium lauryl sulphate, sodium dodecyl sulphate, sodium oleate, sodium ricinoleate, sodium tetradecyl sulphate, sodium hexadecyl sulphate, polyoxyethylene-9-lauryl ethers, glycerol, ethylene glycol, poly-ethylene glycols in molecular range of 300-6000, polyvinylpyrrolidone, sodium glutamate, sodium thiocyanate, 2-bromo-2-nitro-1,3-propanediol, glucose, trehalose, sucrose fatty acid monoesters, sucrose, and cyclodextrins including beta cyclodextrin, hydroxypropyl beta cyclodextrin individually or in a suitable combination thereof.

5. A composition of claim 1, wherein the protein stabilising solute is an anionic surfactant.

6. A composition of claim 1, wherein the protein stabilising solute is sodium lauryl sulphate, sodium dodecyl sulphate, or sucrose.

7. A composition of claim 1, wherein the protein stabilising solute is sodium lauryl sulphate.

8. A composition of claim 1, wherein the composition is a powder or solid.

9. A composition of claim 1, wherein the composition is an aqueous solution.

10. A composition of claim 9, wherein the solution comprises a physiological saline or citrate saline buffer.

* * * * *